United States Patent
Eastman

(10) Patent No.: US 9,057,687 B2
(45) Date of Patent: Jun. 16, 2015

(54) CALIBRATION VIAL AND TECHNIQUE FOR CALIBRATING A FIBER OPTIC OXYGEN SENSING NEEDLE

(75) Inventor: John Eastman, Rogers, MN (US)

(73) Assignee: MOCON, INC., Minneapolis, MN (US)

( * ) Notice: Subject to any disclaimer, the term of this patent is extended or adjusted under 35 U.S.C. 154(b) by 602 days.

(21) Appl. No.: 13/452,226

(22) Filed: Apr. 20, 2012

(65) Prior Publication Data
US 2013/0276508 A1  Oct. 24, 2013

(51) Int. Cl.
| | |
|---|---|
| *G01N 21/63* | (2006.01) |
| *G01N 21/27* | (2006.01) |
| *G01N 21/64* | (2006.01) |
| *G01N 21/77* | (2006.01) |

(52) U.S. Cl.
CPC ............ *G01N 21/278* (2013.01); *G01N 21/643* (2013.01); *G01N 21/77* (2013.01); *G01N 2021/6432* (2013.01)

(58) Field of Classification Search
None
See application file for complete search history.

(56) References Cited

U.S. PATENT DOCUMENTS

| | | | |
|---|---|---|---|
| 3,612,866 A | 10/1971 | Stevens | |
| 4,476,870 A | 10/1984 | Peterson et al. | |
| 4,622,974 A | 11/1986 | Coleman et al. | |
| 4,810,655 A | 3/1989 | Khalil et al. | |
| 4,947,850 A | 8/1990 | Vanderkooi et al. | |
| 5,092,467 A | 3/1992 | Elward | |
| 5,190,729 A | 3/1993 | Hauenstein et al. | |
| 5,230,427 A | 7/1993 | Betts et al. | |
| 5,382,163 A | 1/1995 | Putnam | |
| 5,407,829 A | 4/1995 | Wolfbeis et al. | |
| 5,483,819 A | 1/1996 | Barmore et al. | |
| 5,695,640 A | 12/1997 | Tseng | |
| 5,718,842 A | 2/1998 | Papkovsky et al. | |
| 5,837,865 A | 11/1998 | Vinogradov et al. | |
| 6,060,196 A | 5/2000 | Gordon et al. | |
| 6,074,607 A | 6/2000 | Slovacek et al. | |
| 6,153,701 A | 11/2000 | Potnis et al. | |
| 6,165,741 A | 12/2000 | Wilson et al. | |
| 6,171,368 B1 | 1/2001 | Maget et al. | |
| 6,266,211 B1 | 7/2001 | Thomas, III et al. | |
| 6,330,464 B1 | 12/2001 | Colvin, Jr. et al. | |
| 6,362,175 B1 | 3/2002 | Vinogradov et al. | |
| 6,379,969 B1 | 4/2002 | Mauze et al. | |

(Continued)

FOREIGN PATENT DOCUMENTS

| | | |
|---|---|---|
| CA | 2600563 A1 | 6/2006 |
| EP | 1887344 A1 | 2/2008 |

(Continued)

OTHER PUBLICATIONS

Multisorb Technologies, FRESHPAX, Oxygen Absorbing Packets and Strips, 2009.

(Continued)

*Primary Examiner* — Robert R Raevis
(74) *Attorney, Agent, or Firm* — Sherrill Law Offices, PLLC

(57) ABSTRACT

A calibration tool and method of using the tool to calibrate a fiber optic needle oxygen sensor. The tool includes at least a vial sealingly covered by a septa and containing a supply of particulate oxygen getter within the chamber of the vial. The vial has an open top and is constructed from an oxygen impermeable material. The septa is resealing, needle-penetrable and oxygen impermeable. The supply of particulate oxygen getter is retained within an oxygen permeable sachet.

21 Claims, 1 Drawing Sheet

(56) References Cited

U.S. PATENT DOCUMENTS

| | | |
|---|---|---|
| 6,395,555 B1 | 5/2002 | Wilson et al. |
| 6,689,438 B2 | 2/2004 | Kennedy et al. |
| 6,777,479 B1 | 8/2004 | Bernard et al. |
| 7,135,342 B2 | 11/2006 | Colvin, Jr. et al. |
| 7,138,270 B2 | 11/2006 | Papkovsky et al. |
| 7,368,153 B2 | 5/2008 | Barmore et al. |
| 7,534,615 B2 | 5/2009 | Havens et al. |
| 7,569,395 B2 | 8/2009 | Havens et al. |
| 7,740,965 B2 | 6/2010 | Richards et al. |
| 8,093,055 B2 | 1/2012 | Mayer et al. |
| 2002/0164813 A1 | 11/2002 | Colvin, Jr. et al. |
| 2003/0062262 A1 | 4/2003 | Mansouri et al. |
| 2003/0221477 A1 | 12/2003 | Pierskalla et al. |
| 2003/0235513 A1 | 12/2003 | Asai et al. |
| 2005/0113658 A1 | 5/2005 | Jacobson et al. |
| 2005/0159497 A1 | 7/2005 | Gauthier et al. |
| 2006/0002822 A1 | 1/2006 | Papkovsky et al. |
| 2006/0144811 A1 | 7/2006 | Cheng |
| 2007/0041011 A1 | 2/2007 | Hayden et al. |
| 2007/0212789 A1 | 9/2007 | Havens et al. |
| 2007/0212792 A1 | 9/2007 | Havens et al. |
| 2008/0051646 A1 | 2/2008 | Papkovsky et al. |
| 2008/0072992 A1 | 3/2008 | Baleriaux et al. |
| 2008/0117418 A1 | 5/2008 | Claps et al. |
| 2008/0146460 A1 | 6/2008 | Pollok et al. |
| 2008/0146902 A1 | 6/2008 | Hacker et al. |
| 2008/0148817 A1 | 6/2008 | Miller et al. |
| 2008/0190172 A1 | 8/2008 | Jones |
| 2008/0199360 A1 | 8/2008 | Shahriari |
| 2008/0215254 A1 | 9/2008 | Leiner et al. |
| 2008/0228163 A1* | 9/2008 | Smith ............... 604/411 |
| 2008/0242870 A1 | 10/2008 | Meador et al. |
| 2009/0028756 A1 | 1/2009 | Shahriari |
| 2009/0029402 A1 | 1/2009 | Papkovsky |
| 2009/0075321 A1 | 3/2009 | Obeid et al. |
| 2009/0130700 A1 | 5/2009 | Ince et al. |
| 2009/0297566 A1* | 12/2009 | Brinkman et al. ......... 424/400 |
| 2009/0326344 A1 | 12/2009 | Meyer |
| 2010/0116017 A1 | 5/2010 | Mayer et al. |
| 2011/0136247 A1 | 6/2011 | Papkovsky et al. |
| 2011/0154881 A1 | 6/2011 | Ascheman et al. |
| 2011/0223678 A1 | 9/2011 | Ascheman et al. |

FOREIGN PATENT DOCUMENTS

| | | |
|---|---|---|
| EP | 2336753 A2 | 6/2011 |
| JP | 55-035927 | 3/1980 |
| JP | 2009530785 | 8/2009 |
| WO | 9004268 A1 | 4/1990 |
| WO | 9219150 A1 | 11/1992 |
| WO | 2007120637 A2 | 10/2007 |
| WO | 2010053888 A1 | 5/2010 |

OTHER PUBLICATIONS

Lee, Sang-Kyung et al., "Photoluminescent Oxygen Sensing on a Specific Surface Area Using Phosphorescence 1 Quenching of Pt-Pophyrin", Analytical Sciences, Department of Bioengineering, Tokyo Institute of Technology, pp. D 535-540, Aug. 1997, vol. 13.

Eaton, K. et al., "Effect of Humidity on the Response Characteristics of Iuminescent PtOEP thin Film Optical Oxygen Sensosrs", Sensors & Actuators B, Elsevier Science B. V., vol. 82 pp. 94-104, 2002.

Technical Manual, "Freudenberg Grafted Products", Sep. 2006, pp. 1-32.

Papkovsky, D. et al., "Phosphorescent Sensor Approach for Non-Destructive Measurements of Oxygen in Packaged Foods: Optimisation of Disposable Oxygen Sensors and Their Characterization Over a Wide Temperature Range", Department of Biochemistry, National University of Ireland, Analytical Letters, 33 (9), pp. 1755-1777. 2000.

Austin, E.A.D. et al., "Opto-electronic systems for addressing Ru oxygen sensors: their design optimization and calibration process", Invited Paper, Optoelectronics Research Centre, University of Southampton, Southampton S017IBJ, Oct. 30, 2001.

De Francisci, M. et al., "Real-Time Estimation of Oxygen Concentration in Micro-Nemo-Vessels", Proceedings of the 26th Annual International Conference of the IEEE Embs San Francisco, CA, USA' Sep. 1-5, 2004.

Papkovsky, Dmitri et al., "Biosensors on the basis of luminescent oxygen sensor: the use of microporous light-scattering support materials", Biochemistry Department, National University of Ireland, Cork, Elsevier, 1998. pp. 137-145.

* cited by examiner

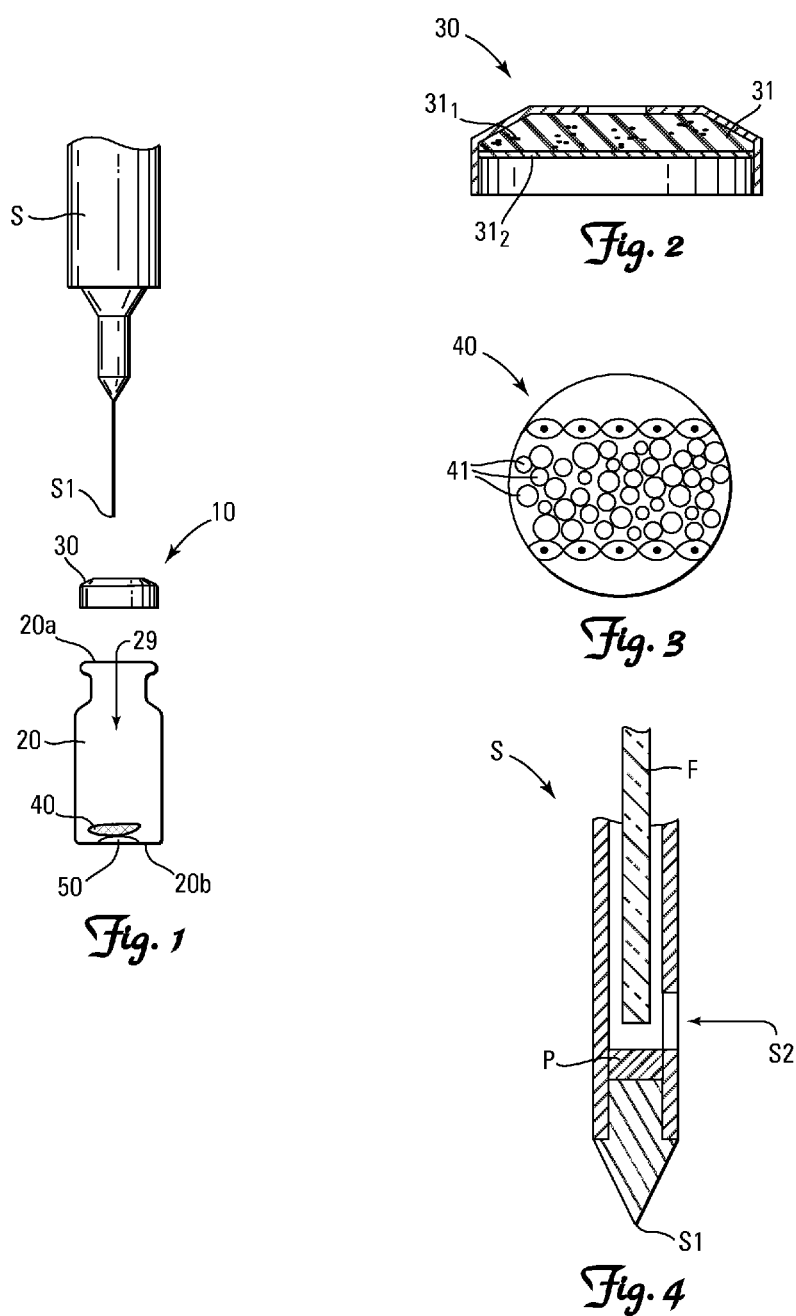

CALIBRATION VIAL AND TECHNIQUE FOR CALIBRATING A FIBER OPTIC OXYGEN SENSING NEEDLE

BACKGROUND

Photoluminescent sensors or probes are a widely employed method of measuring analyte concentration, typically oxygen, within an enclosed space such as a package, container or living tissue. Briefly, analyte concentration within a package or container can be measured by inserting an analyte sensitive photoluminescent probe within the package, container or tissue, allowing the probe to equilibrate within the package, container or tissue, exciting the probe with radiant energy, and measuring the extent to which radiant energy emitted by the excited probe is quenched by the presence of the target analyte. Exemplary optical sensors are described in WO 92/19150 and CA 2,600.563. Such optical sensors are available from a number of suppliers, including Presens Precision Sensing, GmbH of Regensburg, Germany, Oxysense of Dallas, Tex., United States, and Luxcel Biosciences, Ltd of Cork, Ireland.

Analytical instruments used to read such photoluminescent probes are commonly programmed with a calibration mode that permits calibration of the instrument by having the instrument read probes that have been exposed to mediums having known concentrations of the target analyte (e.g., setting the instrument to calibration mode, reading a probe that has been placed within a container that is flushed with certified tank gas containing 0% analyte, and then reading a probe that has been placed within a container that is flushed with certified tank gas containing a known concentration(s) of analyte such as 100% analyte).

While effective for accurately calibrating optical sensors, this calibration method is time consuming and expensive.

Accordingly, a substantial need exists for a low cost system and method for accurately and reliably calibrating instruments used to read photoluminescent sensors or probes.

SUMMARY OF THE INVENTION

A first aspect of the invention is a calibration tool for use in obtaining a zero calibration value for a fiber optic needle oxygen sensor. The calibration tool includes a vial sealingly covered by a septa and containing a supply of particulate oxygen getter within the chamber of the vial. The vial has an open top and is constructed from an oxygen impermeable material. The septa is resealing, penetrable by a fiber optic needle oxygen sensor, and oxygen impermeable. The supply of particulate oxygen getter is retained within an oxygen permeable sachet.

A second aspect of the invention is a method of calibrating a fiber optic needle oxygen sensor having an oxygen sensitive photoluminescent probe proximate the tip of the needle. The calibration method includes the steps of (a) setting the sensor to calibration mode, (b) obtaining a span calibration value by (i) placing the photoluminescent probe on the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and (c) obtaining a zero calibration value by (i) placing the photoluminescent probe on the sensor in fluid communication with the chamber of a calibration tool in accordance with the first aspect of the invention by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

BRIEF DESCRIPTION OF THE DRAWINGS

FIG. 1 is an exploded side view of one embodiment of the invention depicted in combination with a fiber optic needle oxygen sensor.

FIG. 2 is an enlarged cross-sectional side view of the cap component of the invention depicted in FIG. 1.

FIG. 3 is a grossly-enlarged cross-sectional side view of a portion of the sachet component of the invention depicted in FIG. 1 showing the particulate oxygen getter contained within the sachet.

FIG. 4 is a grossly-enlarged cross-sectional side view of the tip of the fiber optic needle oxygen sensor depicted in FIG. 1.

DETAILED DESCRIPTION OF A PREFERRED EMBODIMENT

Definitions

As used herein, including the claims, the phrase "oxygen impermeable" means a material that when formed into a 1 mil (25.4 μm) film has an oxygen transmission rate of less than 10 cm$^3$/m$^2$ day when measured in accordance with ASTM F 1927.

As used herein, including the claims, the phrase "oxygen permeable" means a material that when formed into a 1 mil film has an oxygen transmission rate of greater than 1,000 cm$^3$/m$^2$ day when measured in accordance with ASTM D 3985.

As used herein, including the claims, the phrase "oxygen barrier" means a film, including coated, metalized and multiple layer films, that are impervious to oxygen (such as a layer of metal) or have an oxygen transmission rate of less than 0.1 cm$^3$/m$^2$ day when measured in accordance with ASTM F 1927.

As used herein, including the claims, the phrase "near zero", when used to describe a concentration of oxygen in a sample, means less than 0.01% oxygen.

As used herein, including the claims, the phrase "oxygen sensitivity" or "sensitivity to oxygen" means sensitivity measured by luminescence quenching.

As used herein, including the claims, the phrase "thin film" means a film having a thickness of less than 10 μm.

As used herein, including the claims, the phrase "small container" means a container will a fillable volume of less than 20 ml.

Nomenclature
10 Calibration Tool
20 Vial
20a Open Top of Vial
20b Bottom of Vial
29 Vial Retention Chamber
30 Cap
31 Septa
$31_1$ Resealable Layer of Septa (Elastomer)
$31_2$ Oxygen Barrier Layer of Septa (Metal Foil)
40 Sachet
41 Particulate Oxygen Getter
50 Confirmation Photoluminescent Oxygen Probe
S Fiber Optic Needle Oxygen Sensor
$S_1$ Tip of Fiber Optic Needle Oxygen Sensor
$S_2$ Side Port In Fiber Optic Needle Oxygen Sensor F Fiber Optic Filament
P Photoluminescent Oxygen Probe Construction FIG. 1 depicts a calibration tool 10 constructed in accordance with the invention. The calibration tool 10 includes a vial 20, a cap 30 and a sachet 40 containing a particulate oxygen getter 41.

The vial 20 or other suitable container has an open top 20a and a closed bottom 20b. The vial 20 preferably has a fillable volume of less than 50 ml, with a preference for small containers having a fillable volume of between 2 and 20 ml.

The vial 20 can be constructed from substantially any oxygen impermeable material possessing the necessary structural integrity. The vial 20 is preferably constructed from an oxygen barrier material for reducing the rate at which oxygen permeates through the walls of the vial 20 and into the chamber 29 defined by the vial 20. Suitable materials include specifically, but not exclusively, glass and certain plastics. Glass is preferred.

Referring to FIGS. 1 and 2, the open top 20a of the vial 20 is sealingly covered by a cap 30 with a septa 31 or other suitable sealing device. In addition to sealing off the chamber 29 of the vial 20 from the surrounding environment, the cap 30, and in particular the septa 31 on the cap 30, needs to be impermeable to oxygen—at least prior to being penetrated by the tip $S_1$ of a fiber optic needle oxygen sensor S, and reseal after being penetrated by the tip $S_1$ of a fiber optic needle oxygen sensor S. Use of a cap 30 which is not impermeable to oxygen can significantly reduce the useful lifespan of the calibration tool 10 by rapidly utilizing the oxygen getter retained within the chamber 29 even prior to use, and in egregious cases can transmit oxygen at a rate faster than the ocygen getter 41 retained within the chamber 29 can scavenge the oxygen, causing the oxygen concentration within the chamber 29 to almost instantaneously rise well above zero. Use of a cap 30 which cannot reseal after being penetrated by the tip $S_1$ of a fiber optic needle oxygen sensor S effectively renders the calibration tool 10 an expensive single use disposable item as oxygen from the surrounding environment will readily pass through the hole left in the cap 30 after a single fiber optic needle oxygen sensor S is calibrated with the calibration tool 10.

Referring to FIG. 2, one type of cap 30 capable of providing both the desired resealing and oxygen impermeable characteristics is a cap 30 with a septa 31 comprised of a layer of resealing elastomer $31_1$, such as synthetic silicone rubber, with a layer of an oxygen impermeable material $31_2$, such as a metal foil, laminated to the underside thereof. Caps 30 with such dual functional septa 31 are available from a number of sources, including Sigma-Aldrich and Fisher Scientific. The cap 30 can be selected from any style cap including specifically, but not exclusively screw and crimp style caps, with crimp style caps generally preferred.

Referring to FIGS. 1 and 3, particulate oxygen getter 41 is provided within the chamber 29 of the vial 20 for consuming any oxygen that reaches the chamber 29 through the vial 20 and/or the cap 30 in order to maintain the concentration of oxygen within the chamber 29 at near zero.

The oxygen getter 41 can be selected from any known oxygen getter, including specifically but not exclusively activated carbon, silica gel, activated alumina, molecular sieve, metals such as iron, magnesium, zinc and titanium, and various inorganic salts of such metals.

As is known to those of routine skill in the art, a particulate hygroscopic material (not shown) is frequently employed in combination with a particulate oxygen getter 41 as many oxygen getters 41 require water in order to chemically react with and scavenge the oxygen, and water absorbed by a hygroscopic material can provide the necessary supply of water.

The oxygen getter 41 must have an oxygen consumption rate that exceeds the permeation rate of oxygen into the chamber 29 from the surrounding air. Generally, the oxygen getter 41 preferably consumes oxygen at a rate that is only slightly greater than the permeation rate of oxygen into the chamber 29, with a generally acceptable range of between two to ten times the permeation rate of oxygen into the chamber 29. One of the factors that impacts the speed with which the oxygen getter 41 can scavenge oxygen within the chamber 29 is the surface area of the oxygen getter 41. In order to provide a surface area effective for scavenging oxygen reaching the chamber 29 at a rate that is at least as fast as the rate at which oxygen permeates into the chamber 29 from the surrounding air, the oxygen getter 41 is preferably provided in particulate or powdered form with an average particle size of less than 10 mil, preferably 1-5 mil and most preferably 1-3 mil. However, when provided in this form I discovered that the particulates have a tendency to diffuse into and coat the probe P and fiber optic filament F on fiber optic needle oxygen sensors S inserted into the chamber 29 containing these particulates, with a concomitant reduction in the accuracy and sensitivity of the contaminated sensor S. Referring to FIGS. 1 and 3, I discovered that this drawback could be eliminated, without significantly impacting the oxygen scavenging performance of the particulate oxygen getter 41, by retaining the oxygen getter 41 in an oxygen permeable sachet 40. Such sachets 40 filled with particulate ocygen getter material 41 are commercially available from a number of suppliers, typically sold for purposes of protecting packaged foods, including Multisorb Technologies under the designation FreshPax®.

The outside of the vial 20 can be imprinted with indicia (not shown) identifying the vial 20 as a zero-calibration tool 10 (e.g., "0% $O_2$", "Zero $O_2$", etc.).

One of the factors impacting the lifespan of the calibration tool 10 is the ratio of oxygen getter 41 to chamber size 29. A lifespan of at least one year from sealing of the chamber 29 or 100 uses, whichever occurs first, is generally desired. In order to reach this desired lifespan, a weight/volume ratio of oxygen getter 41 to sealed chamber 29 of 1:5 to 1:20 mg/cm$^3$ is generally effective, with a weight/volume ratio of 1:10 to 1:20 mg/cm$^3$ generally preferred.

The calibration tool 10 can optionally be equipped with a confirmation probe 50 within the chamber 29 for allowing the oxygen concentration within the chamber 29 to be checked by interrogating the confirmation probe 50 with a photoluminescent reader (not shown).

Vials 20 equipped with a confirmation probe 50 within the chamber 29 need to be transparent or translucent at least at the specific wavelengths at which the confirmation probe 50 absorbs and emits energy.

The oxygen sensitive confirmation probe 50 can be constructed in accordance with standard convention by embedding an oxygen-sensitive photoluminescent dye (not shown) within an oxygen-permeable carrier matrix (not shown).

The oxygen-sensitive photoluminescent dye (not shown) may be selected from any of the well-known oxygen sensitive photoluminescent dyes used in the construction of oxygen sensitive photoluminescent probes. A nonexhaustive list of such oxygen sensitive photoluminescent dyes (not shown) includes specifically, but not exclusively, ruthenium(II)-bipyridyl and ruthenium(II)-diphenylphenanothroline complexes, porphyrin-ketones such as platinum(II)-octaethylporphine-ketone, platinum(II)-porphyrin such as platinum(II)-tetrakis(pentafluorophenyl)porphine, palladium(II)- porphyrin such as palladium(II)-tetrakis(pentafluorophenyl) porphine, phosphorescent metallocomplexes of tetrabenzoporphyrins, chlorins, azaporphyrins, and long-decay luminescent complexes of iridium(III) or osmium(II).

Compositions suitable for use as the carrier matrix (not shown) are oxygen-permeable compositions, preferably highly oxygen permeable compositions. One of routine skill in the art is capable of selecting such oxygen-permeable carrier compositions (not shown). A nonexhaustive list of polymers suitable for use as the carrier matrix (not shown) includes specifically, but not exclusively, silicone, polystryrene, polycarbonate, polysulfone, and some other polymers and co-polymers.

Use

The calibration tool 10 can be used to quickly and easily calibrate a fiber optic needle oxygen sensor S having an onboard oxygen sensitive photoluminescent probe P and programmed with a calibration mode. Calibration of the sensor S simply involves the steps of (1) setting the sensor S to calibration mode, (2) obtaining a span calibration value by (i) placing the photoluminescent probe P on the sensor S in fluid communication with a fluid having a known non-zero partial pressure of oxygen (typically atmospheric air known to have a stable concentration of 20.95% $O_2$), (ii) taking an oxygen concentration reading with the photoluminescent probe P onboard the sensor S in fluid communication with such fluid, and (iii) correlating the oxygen concentration reading with the known non-zero oxygen partial pressure, and (3) obtaining a zero calibration value by (i) placing the photoluminescent probe P onboard the sensor S in fluid communication with the chamber 29 of a calibration tool 10 by inserting the tip of the needle $S_1$ through the septa 31 covering the chamber 29, (ii) taking an oxygen concentration reading with the photoluminescent probe P in fluid communication with the contents of the chamber 29, and (iii) correlating the oxygen concentration reading with the known near zero oxygen partial pressure in the chamber 29.

Correlation of each oxygen concentration reading to the proper calibration point (i.e., span calibration reading or zero calibration reading) can be accomplished in various ways. One technique is to take the oxygen concentration readings in a predetermined sequence previously input into the optical oxygen sensor S. A second technique is to provide the optical oxygen sensor S with additional data each time a reading is taken effective for indicating which calibration point has been or will be taken. A third technique is to provide the optical oxygen sensor S with additional data each time a reading is taken effective for indicating the oxygen concentration to which probe P was exposed at the time of the reading (e.g., user input of 20.95% $O_2$ after reading air and 0% $O_2$ after reading the chamber 29 of the calibration tool 10.).

I claim:

1. A calibration tool for use in obtaining a zero calibration value for a fiber optic needle oxygen sensor, comprising:
   (a) an open top vial constructed from an oxygen impermeable material and defining a chamber,
   (b) a resealing, needle-penetrable, oxygen impermeable septa sealingly engaged over the open top of the vial,
   (c) an oxygen permeable sachet containing a mass of particulate oxygen getter retained within the sealed chamber, and
   (d) a mass of an oxygen sensitive photoluminescent dye retained within and in fluid communication with the sealed chamber.

2. A method of calibrating a fiber optic needle oxygen sensor having an oxygen sensitive photoluminescent probe proximate the tip of the needle, comprising the steps of:
   (a) setting the sensor to calibration mode,
   (b) obtaining a span calibration value by (i) placing the photoluminescent probe of the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and
   (c) obtaining a zero calibration value by (i) placing the photoluminescent probe of the sensor in fluid communication with the chamber of the calibration tool of claim 1 by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

3. The method of claim 2 wherein the span calibration value and the zero calibration value are taken in a predetermined sequence.

4. The method of claim 2 further comprising the step of providing the oxygen sensor with data indicating whether a first reading was a span calibration value or a zero calibration value.

5. The method of claim 2 wherein the span calibration value is obtained by placing the photoluminescent probe in fluid communication with the atmosphere.

6. The calibration tool of claim 1, wherein the oxygen getter is iron.

7. A method of calibrating a fiber optic needle oxygen sensor having an oxygen sensitive photoluminescent probe proximate the tip of the needle, comprising the steps of:
   (a) setting the sensor to calibration mode,
   (b) obtaining a span calibration value by (i) placing the photoluminescent probe of the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and
   (c) obtaining a zero calibration value by (i) placing the photoluminescent probe of the sensor in fluid communication with the chamber of a calibration tool in accordance with claim 6 by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

8. The calibration tool of claim 6, wherein the iron is an iron powder having an average particle size of 1 to 5 mil.

9. The calibration tool of claim 6, wherein the weight/volume ratio of iron/ sealed chamber is 1:10 to 1:20 mg/cm$^3$.

10. A method of calibrating a fiber optic needle oxygen sensor having an oxygen sensitive photoluminescent probe proximate the tip of the needle, comprising the steps of:
    (a) setting the sensor to calibration mode,
    (b) obtaining a span calibration value by (i) placing the photoluminescent probe of the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and (c) obtaining a zero calibration value by (i) placing the photoluminescent probe of the sensor in fluid communication with the chamber of a calibration tool in accordance with claim 9 by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

11. The calibration tool of claim 1, wherein the vial is a glass vial.

12. The calibration tool of claim 1, wherein the vial is a small container.

13. A calibration tool for use in obtaining a zero calibration value for a fiber optic needle oxygen sensor, comprising:
   (a) an open top vial constructed from an oxygen impermeable material and defining a chamber,
   (b) a resealing, needle-penetrable, oxygen impermeable septa sealingly engaged over the open top of the vial, and
   (c) an oxygen permeable sachet containing a mass of particulate oxygen getter retained within the sealed chamber,
   (d) wherein the septa includes an oxygen barrier layer laminated to a layer of resealing elastomer.

14. A method of calibrating a fiber optic needle oxygen sensor having an oxygen sensitive photoluminescent probe proximate the tip of the needle, comprising the steps of:
   (a) setting the sensor to calibration mode,
   (b) obtaining a span calibration value by (i) placing the photoluminescent probe of the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and
   (c) obtaining a zero calibration value by (i) placing the photoluminescent probe of the sensor in fluid communication with the chamber of a calibration tool in accordance with claim 13 by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

15. The method of claim 14 wherein the span calibration value and the zero calibration value are taken in a predetermined sequence.

16. The method of claim 14 further comprising the step of providing the oxygen sensor with data indicating whether a first reading was a span calibration value or a zero calibration value.

17. The method of claim 14 wherein the span calibration value is obtained by placing the photoluminescent probe in fluid communication with the atmosphere.

18. The calibration tool of claim 13, wherein the oxygen barrier layer is aluminum foil.

19. A method of calibrating a fiber optic needle oxygen sensor having an oxygen sensitive photoluminescent probe proximate the tip of the needle, comprising the steps of:
   (a) setting the sensor to calibration mode,
   (b) obtaining a span calibration value by (i) placing the photoluminescent probe of the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and
   (c) obtaining a zero calibration value by (i) placing the photoluminescent probe of the sensor in fluid communication with the chamber of a calibration tool in accordance with claim 18 by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

20. The calibration tool of claim 13, wherein the elastomer is a synthetic silicone rubber.

21. A method of calibrating a fiber optic needle oxygen sensor having an oxygen sensitive photoluminescent probe proximate the tip of the needle, comprising the steps of:
   (a) setting the sensor to calibration mode,
   (b) obtaining a span calibration value by (i) placing the photoluminescent probe of the sensor in fluid communication with a fluid having a known non-zero partial pressure of oxygen, (ii) taking an oxygen concentration reading with the photoluminescent probe in fluid communication with a fluid having a known non-zero partial pressure of oxygen, and (iii) correlating the oxygen concentration reading with the known non-zero oxygen partial pressure, and
   (c) obtaining a zero calibration value by (i) placing the photoluminescent probe of the sensor in fluid communication with the chamber of a calibration tool in accordance with claim 20 by inserting the needle through the septa on the calibration tool, (ii) taking an oxygen concentration reading with the photoluminescent probe in fluid communication with the chamber of the calibration tool, and (iii) correlating the oxygen concentration reading with the known near zero oxygen partial pressure in the chamber.

* * * * *